US005681270A

United States Patent [19]
Klearman et al.

[11] Patent Number: 5,681,270
[45] Date of Patent: Oct. 28, 1997

[54] ORTHOTIC APPARATUS FOR PROVIDING ABDUCTION A PATEINT'S LEGS

[75] Inventors: Jeffrey D. Klearman, St. Louis; Jerry M. Roth, House Springs; Matt Roth; Robert T. Bronson, both of St. Louis, all of Mo.

[73] Assignee: Therapy Concepts, Inc., St. Louis, Mo.

[21] Appl. No.: 534,833

[22] Filed: Sep. 27, 1995

[51] Int. Cl.⁶ ........................................ A61F 5/00
[52] U.S. Cl. .................. 602/24; 602/23; 128/845; 128/847
[58] Field of Search ..................... 602/19, 23, 24, 602/5, 13; 128/845, 846, 882, DIG. 20; 5/648

[56] References Cited

U.S. PATENT DOCUMENTS

| | | |
|---|---|---|
| 4,372,299 | 2/1983 | Fixel ........................................ 602/24 |
| 4,497,315 | 2/1985 | Fettweis et al. |
| 4,727,861 | 3/1988 | Yeomans et al. |
| 4,881,532 | 11/1989 | Borig et al. |
| 5,205,814 | 4/1993 | Lundrigen et al. ........................ 602/19 |
| 5,289,828 | 3/1994 | Toth ........................................ 602/24 X |
| 5,558,628 | 9/1996 | Bzoch ...................................... 128/182 X |

OTHER PUBLICATIONS

Brochure of Orthosis Corrective Systems, Inc., OSCAR HKO, dated before Sep. 1994.

*Primary Examiner*—Richard J. Apley
*Assistant Examiner*—Kim M. Lee
*Attorney, Agent, or Firm*—Howell & Haferkamp, L.C.

[57] ABSTRACT

An orthosis for providing abduction to a patient's legs comprises first and second leg engaging portions configured for operatively engaging first and second legs of the patient and at least one inflatable bladder generally between and operatively attached to the leg engaging portions. The bladder has at least one port for introducing fluid into and removing fluid from the bladder thereby to inflate and deflate the bladder. The bladder is positioned relative to the first and second leg engaging portions so that the bladder resists movement of the leg engaging portions toward each other when the bladder is inflated to maintain the first and second leg engaging portions spaced apart and thereby to maintain the legs of a patient wearing the orthosis spread apart.

25 Claims, 5 Drawing Sheets

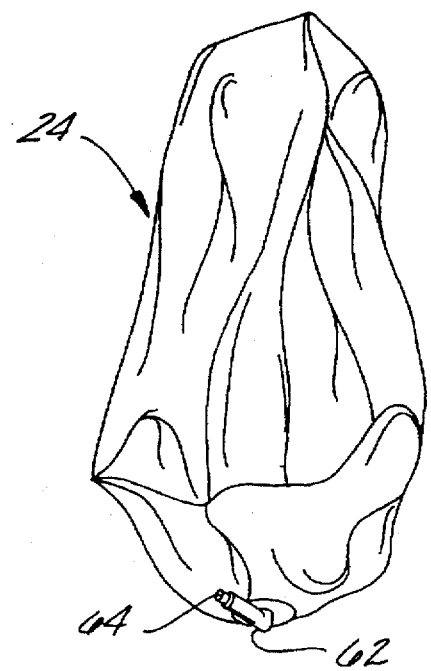
FIG. 5
FIG. 6
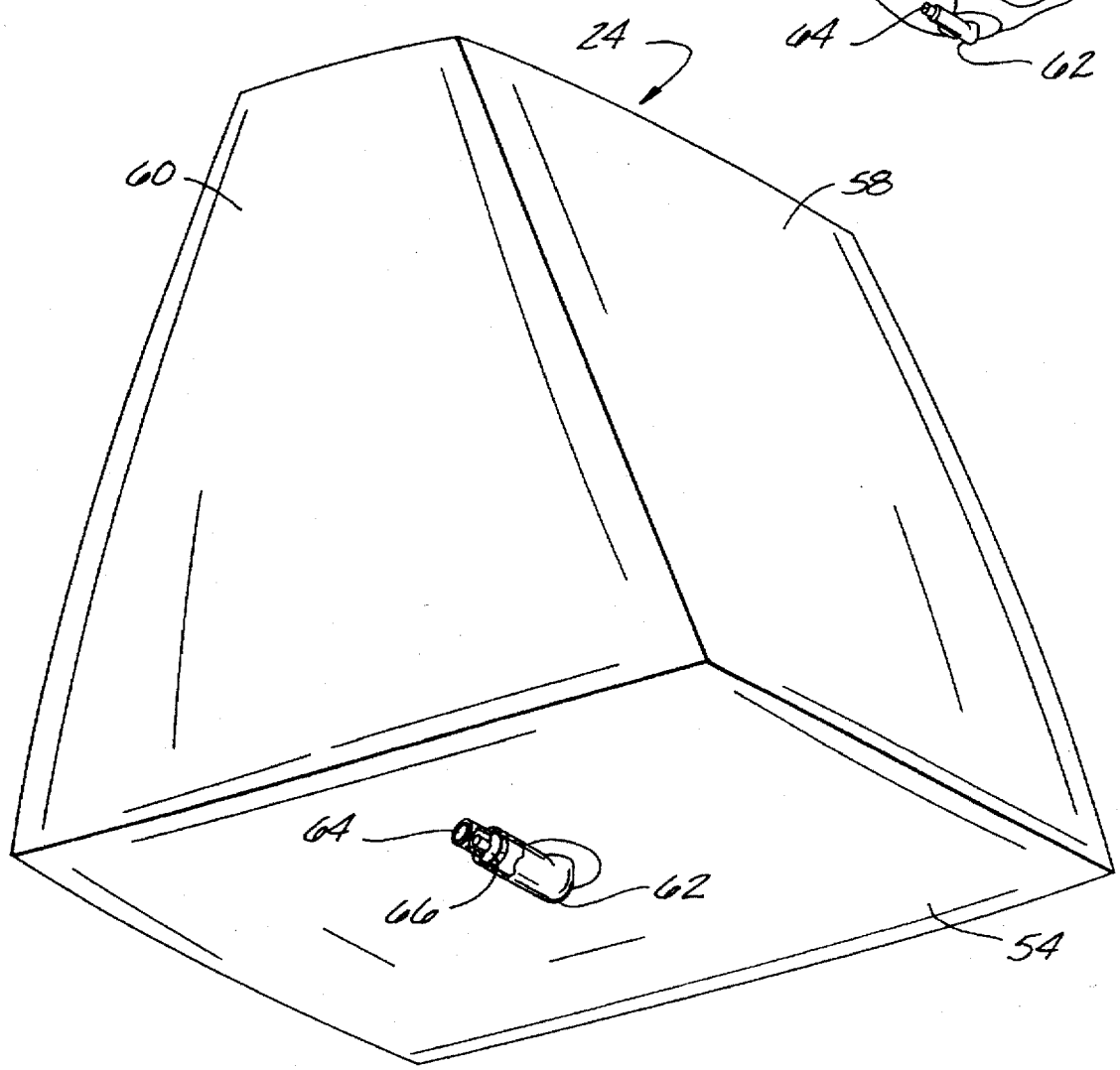

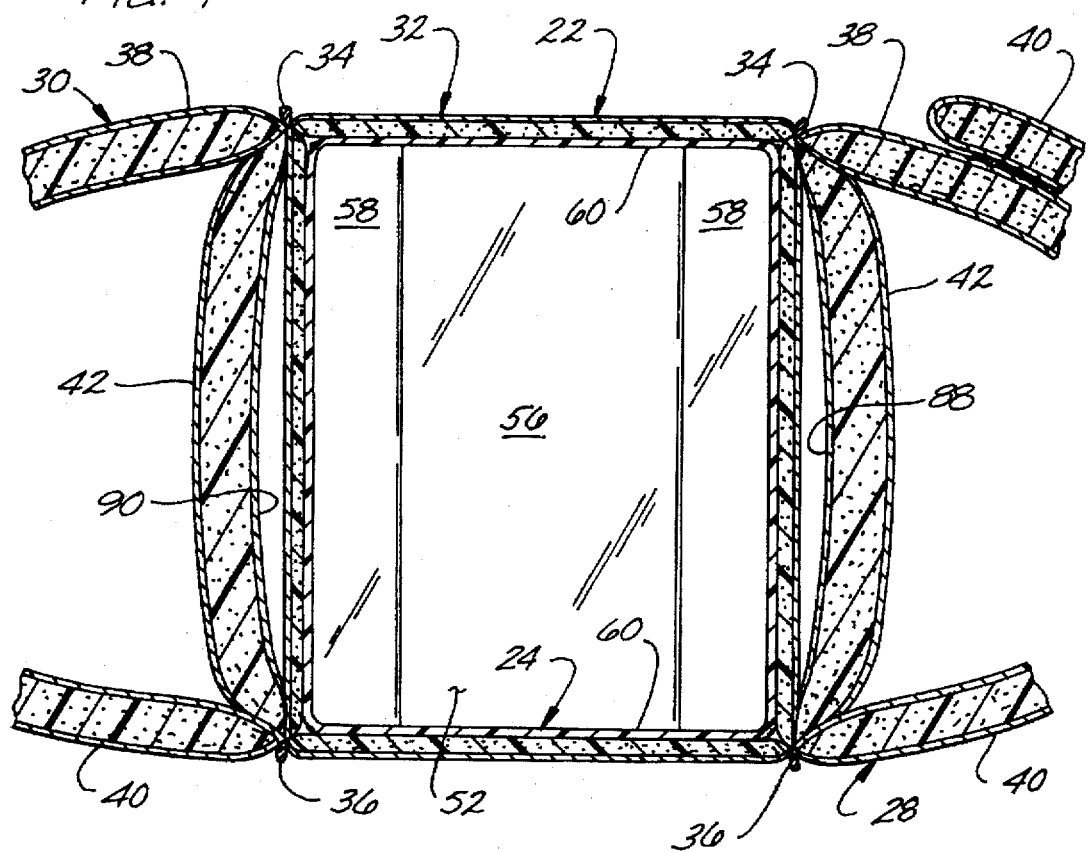
FIG. 7
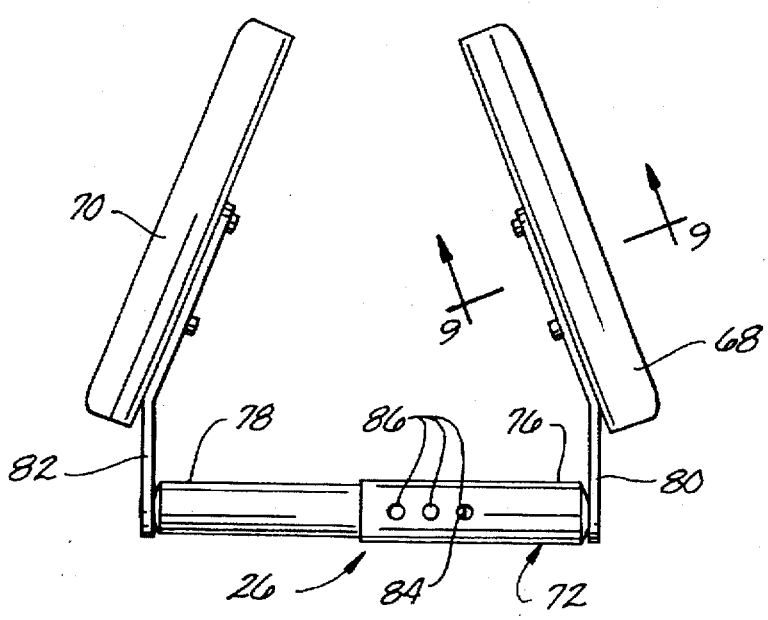
FIG. 8
FIG. 9

ORTHOTIC APPARATUS FOR PROVIDING ABDUCTION A PATEINT'S LEGS

BACKGROUND OF THE INVENTION

This invention relates generally to orthotic devices and more particularly to orthotic devices for providing abduction to legs of a patient.

A conventional hip and knee orthosis ("HKO") is used primarily by patients suffering from contractures of leg muscles. A contracture is a shortening of a muscle which produces distortion or deformity or abnormal limitation of movement of a joint. Contractures of the legs often force the patient's legs together, causing the knees or other portions of the legs to rub together and thereby abrade the skin. Contractures are often treated by providing abduction to the legs. HKOs provide abduction to the legs by urging the legs outward and away from the longitudinal axis of the patient's body.

HKOs are also used to immobilize the patient's hip after hip surgery.

One type of HKO has a rigid brace extending between and strapped to the thighs of a patient for separating the legs. In such an HKO the brace is adjustable to vary the spacing (or angle) of the legs. A disadvantage associated with such an HKO is that the rigid brace provides a localized pressure (uneven pressure distribution) to the thighs of the patient. This localized pressure may cause discomfort to the patient and may induce ulcerations of the skin.

Another type of HKO uses a wedge-shaped member formed of a resilient foam material. The wedge-shaped member is positioned between the thighs of the patient to maintain the legs spread apart. A disadvantage of this type of HKO is that the degree (angle) of abduction can be adjusted only by replacing the wedge-shaped member with a member of a different size or resiliency. Also, insertion of this type of HKO often causes increased pain and discomfort to the patient because the patient's legs must be initially spread wider than the HKO to accommodate its insertion. Further, the wedge-shaped members are difficult to clean.

SUMMARY OF THE INVENTION

Among the several objects of the present invention may be noted the provision of an improved orthosis for providing abduction to the legs of a patient; the provision of such an orthosis which avoids localized pressure points; the provision of such an orthosis which requires only a minimal spread of the patient's legs during insertion of the orthosis; the provision of such an orthosis in which the degree of abduction of the patient's legs is readily adjusted; the provision of such an orthosis which is easy to clean and maintain; and the provision of such an orthosis which is of relatively simple construction.

In general, an orthosis of the present invention for providing abduction to legs of a patient comprises first and second leg engaging portions configured for operatively engaging first and second legs of the patient and at least one inflatable expandable bladder generally between and operatively attached to the leg engaging portions. The bladder has at least one port for introducing fluid into and removing fluid from the bladder thereby to inflate and deflate the bladder. The bladder is positioned relative to the first and second leg engaging portions so that the bladder resists movement of the leg engaging portions toward each other when the bladder is inflated to maintain the first and second leg engaging portions spaced apart and thereby to maintain the legs of a patient wearing the orthosis spread apart.

In another aspect of the present invention, a method of providing abduction to legs of a patient comprises engaging first and second legs of the patient with first and second leg engaging portions of an orthosis. The orthosis has at least one inflatable bladder generally between the first and second leg engaging portions. Fluid is introduced into the bladder to inflate the bladder. The first and second leg engaging portions are spaced-apart by the bladder when the bladder is inflated for maintaining the legs of the patient spread apart.

Other objects and features will be in part apparent and in part pointed out hereinafter.

BRIEF DESCRIPTION OF THE DRAWINGS

FIG. 5 is a perspective view of the bladder of FIG. 3 in a deflated condition;

FIG. 6 is an enlarged perspective view of the bladder of FIG. 5 in an inflated condition and with portions of an inflation stem thereof broken away to show detail;

FIG. 7 is a fragmented sectional view similar to the view of FIG. 4, but showing the leg engaging portions and bladder when the orthosis is not being worn by a patient;

FIG. 8 is a top plan view of the brace structure of FIG. 1; and

FIG. 9 is a cross-sectional view taken along the plane of line 9—9 of FIG. 8.

Corresponding reference characters indicate corresponding parts throughout the several views of the drawings.

DESCRIPTION OF THE PREFERRED EMBODIMENTS

Figure 1:
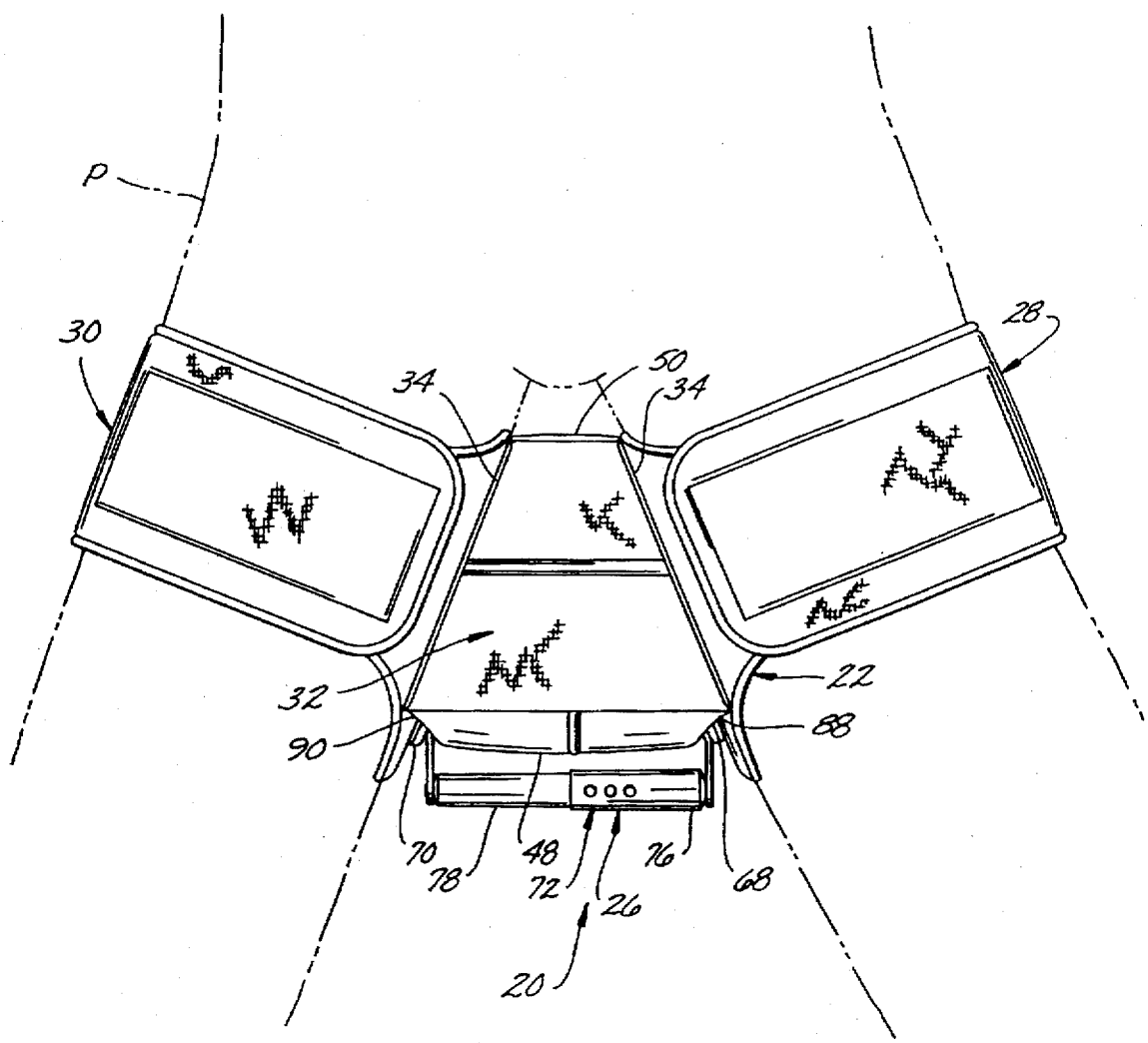
FIG. 1 is a top plan view of an orthosis of the present invention showing an orthosis body and a brace structure bracing the orthosis body.
Figure 2:
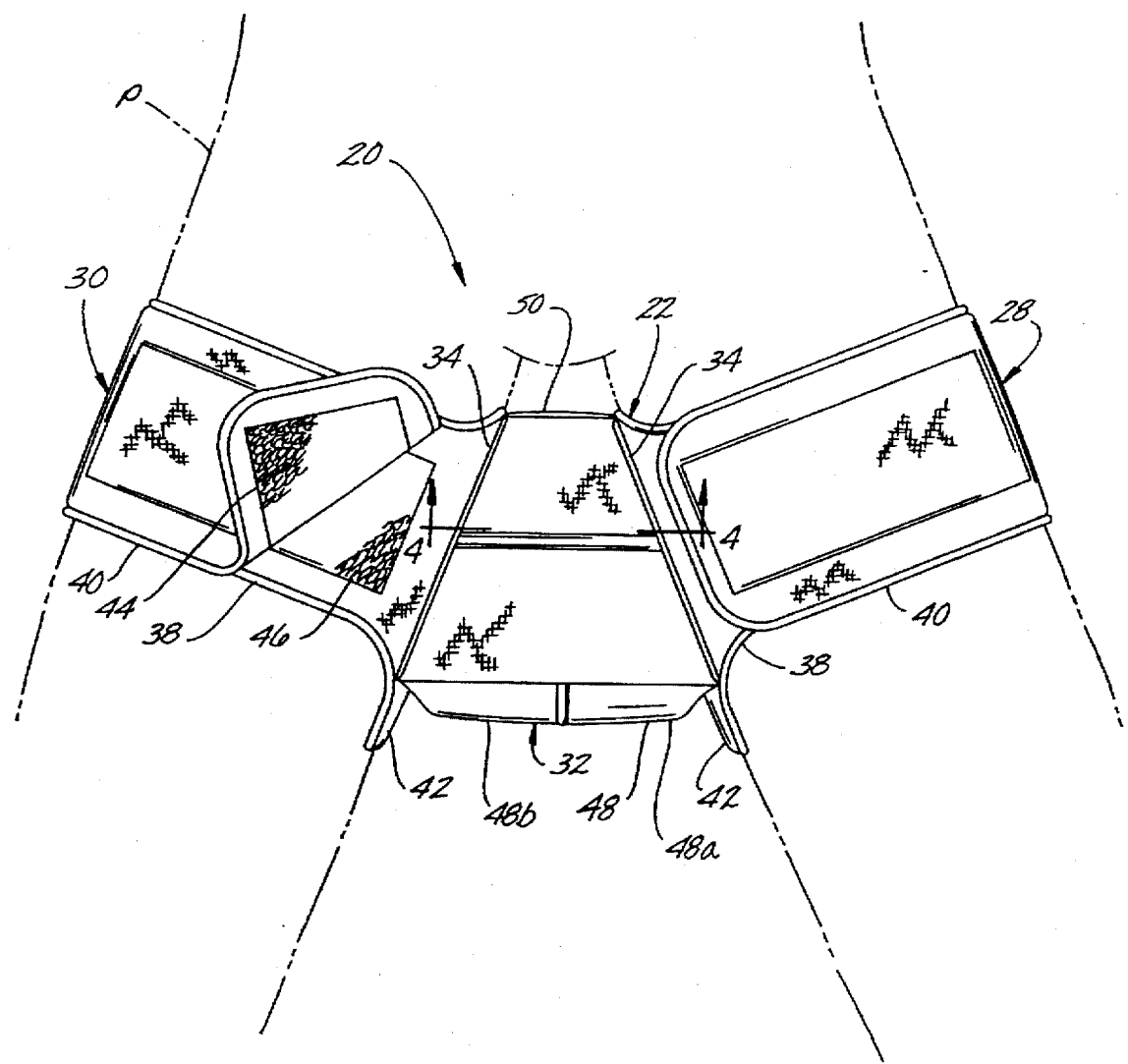
FIG. 2 is a top plan view of the orthosis of FIG. 1 but with a brace structure removed from the orthosis body.
Figure 3:
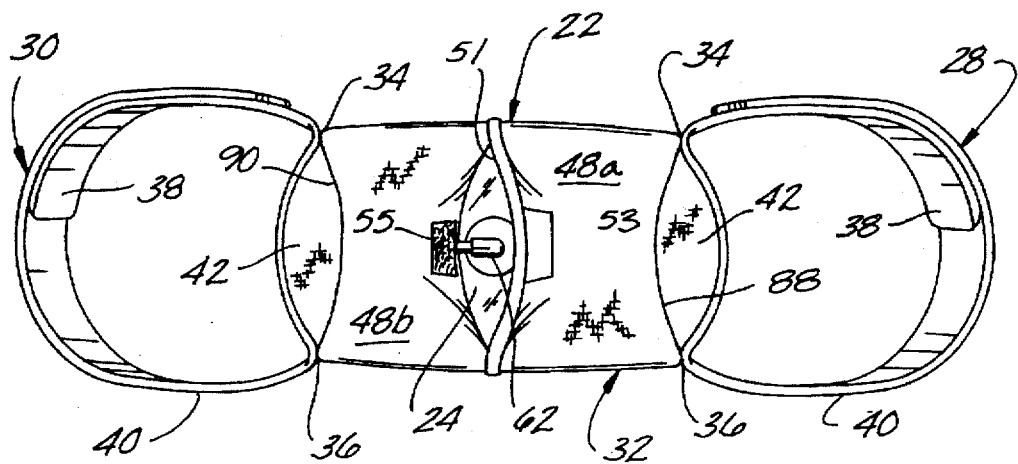
FIG. 3 is a front elevational view of the orthosis of FIG. 2 showing an inflatable expandable bladder within the orthosis body.
Figure 4:
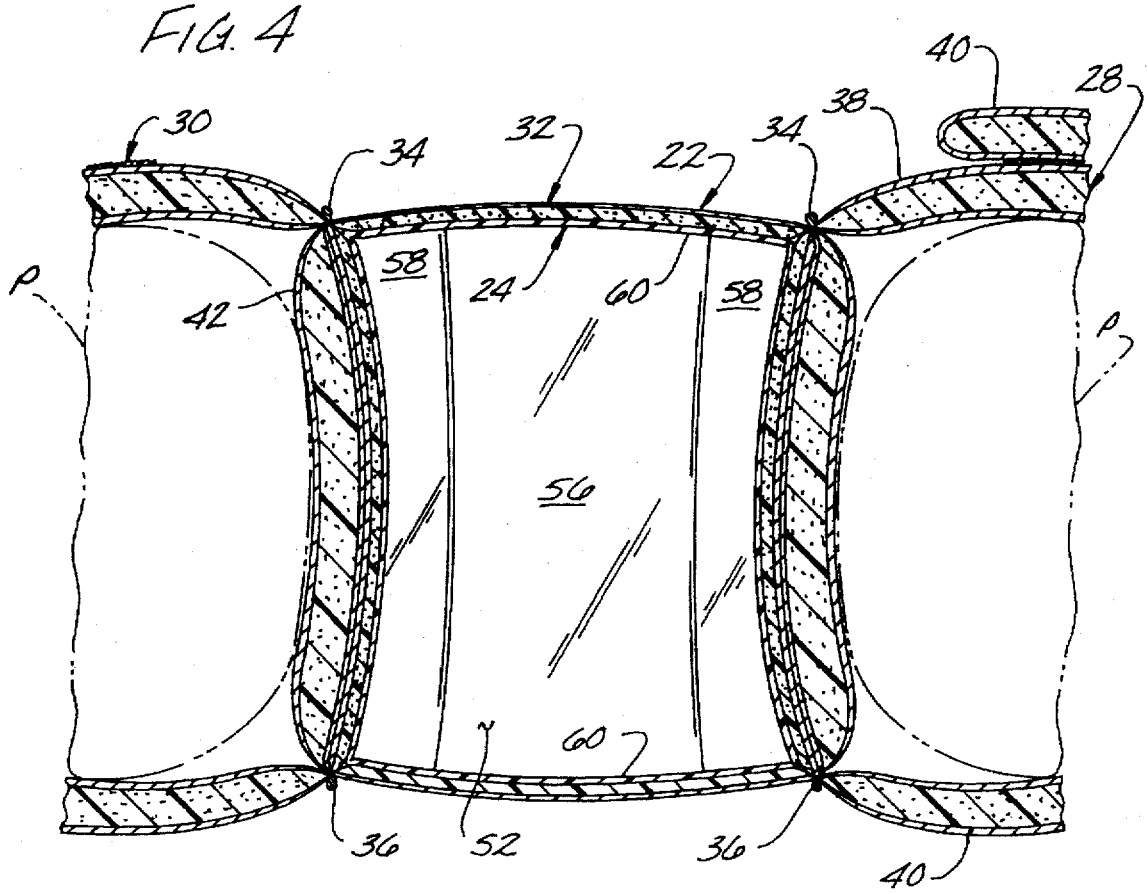
FIG. 4 is a fragmented cross-sectional view taken along the plane of line 4—4 of FIG. 2 showing leg engaging portions of the orthosis body and the bladder conforming to the shape of a patient's legs when the orthosis is being worn by the patient.

Referring now to the drawings, and first more particularly to FIGS. 1-4, a hip-knee orthosis of the present invention is indicated in its entirety by the reference numeral 20. The orthosis 20 is configured for providing abduction to legs of a patient. It comprises an orthosis body 22, an inflatable expandable bladder 24, and a brace structure The orthosis body 22 is preferably formed of multiple sheets of flexible material joined together as by stitching. It includes left and right leg (or thigh) engaging portions 28, 30, and a bladder receiving pocket 32 generally between the leg engaging portions for holding the bladder 24. The leg engaging portions 28, 30 are configured for operatively engaging left and right legs of a patient P (shown in phantom in FIGS. 1 and Preferably, the leg engaging portions 28, 30 engage the thighs of the patient P. As shown in FIGS. 2-4, each leg engaging portion 28, 30 is an elongated flexible member stitched along upper and lower seams 34, 36 (FIG. 3) to the bladder receiving pocket 32. Preferably, the leg engaging portions are formed of a foam padding surrounded by a suitable breathable fabric material for minimizing discomfort to the patient. The seams 34, 36 divide each leg engaging portion 28, 30 into three sections: a relatively short flap 38 extending generally outward from the upper seam, a relatively long strap 40 extending generally outward from the lower seam, and an intermediate portion 42 extending from the upper seam downward to the lower seam. The straps 40 are adapted to be looped around the legs of the patient P so that end margins of the straps overlap the flaps 38. As shown in FIG. 2, hook-type fasteners 44 on the straps 40 are adapted to mate with loop-type fasteners 46 on the flaps 38 to releasably fasten the straps to the flaps to thereby secure the orthosis body 22 to the legs of the patient.

The bladder receiving pocket 32 attaches the bladder 24 to the leg engaging portions 28, 30. It preferably comprises a plurality of sheets of flexible material stitched together to form a soft-walled box which tapers from a wide end wall 48 (facing generally downward as viewed in FIGS. 1 and 2 toward the knees of the patient) to a narrow end wall 50 (facing generally upward toward the pelvis of the patient). The bladder receiving pocket 32 defines a bladder receiving chamber 52 (FIG. 4) for receiving the inflatable bladder 24. The wide end wall 48 has first and second portions (panels) 48a, 48b (FIG. 3). The panels define an opening 51 through the wide end wall 48 to facilitate insertion of the bladder 24 into and removal of the bladder from the bladder receiving chamber 52. Preferably, the opening 51 is sufficiently large to permit insertion and removal of the bladder 24 when the bladder is in a deflated (i.e., collapsed) condition (shown in FIG. 5) and sufficiently small to prevent insertion and removal of the bladder when the bladder is in an inflated condition (shown in FIG. 6). First and second mateable fastener elements 53, 55 (FIG. 3), such as mateable hook- and loop-type fasteners, are attached to the first and second panels 48a, 48b to releasably hold the first and second panels together. Thus, the opening 51 is closed when the fastener elements 53, 55 engage one another.

The bladder 24 is of relatively thin-walled construction and is sized and shaped for filling the bladder receiving chamber 52 of the bladder receiving pocket 32. It includes a wide end wall 54, a narrow end wall 56 (FIGS. 4 and 7) opposite the wide end wall, two generally rectangular side walls 58 joined along end edges to the end walls, and two tapered side walls 60 joined along end edges to the end walls and joined along side edges to the rectangular-shaped side walls. Preferably, when the bladder 24 is in an inflated condition (as shown in FIG. 6) it is wedge-shaped. The walls of the bladder 24 are preferably of a flexible polymeric sheet material, such as polyvinyl chloride. Also preferably, the walls are of generally low elasticity to minimize stretching of the walls so that the wedge-shape is substantially maintained even when the bladder 24 is over-inflated. When the bladder 24 is positioned within the bladder receiving pocket 32 and inflated, it resists inward movement of the leg engaging portions 28, 30 (i.e., movement of the leg engaging portions toward each other) to maintain the legs of a patient wearing the orthosis 20 spread apart. Because of the construction of the bladder 24, increasing the inflation of the bladder (i.e., adding fluid thereto) increases resistance of movement of the leg engaging portions 28, 30 toward each other and decreasing the inflation of the bladder (i.e., removing fluid therefrom) decreases resistance of movement of the leg engaging portions toward each other.

In the preferred embodiment, the orthosis 20 has only one bladder 24. It is to be understood however that the bladder could be replaced with two or more smaller bladders without departing from the scope of this invention. Alternatively, the bladder could have two or more independently inflatable cells arranged in a side-by-side configuration. By varying the number of cells that are inflated, the shape of the bladder (e.g., the size of the wedge formed by the bladder) can be varied to meet the particular needs of the patient.

Referring now to FIGS. 3, 5, and 6, an inflation/deflation stem 62 is attached to the wide end wall 54 of the bladder 24. The stem 62 is hollow and has a port 64 for introducing fluid (e.g., air) into and removing fluid from the inside of the bladder 24 to inflate and deflate the bladder. A valve piston 66 (FIG. 6) within the stem 62 is slidable between an open position and a closed position. When the valve piston 66 is in its open position, air can be introduced into and removed from the bladder 24. When the valve piston 66 is in its closed position, it seals an opening through the stem 62 to block air flow through the stem. The bladder may be filled with a suitable hand pump (not shown), such as a conventional bicycle pump. During inflation, air pressure at the pump side of the stem 62 is greater than air pressure within the bladder 24, thereby causing the valve piston 66 to move to its open position. After inflation (i.e., after disconnection of the pump), air pressure within the bladder biases the valve piston 66 to its closed position. To deflate the bladder 24, a thin rod (not shown) or other suitable tool may be inserted through the port 64 of the stem 62 to manually move the valve piston 66 to its open position.

Although the bladder 24 preferably has only one inflation/deflation stem, it is to be understood that the bladder could be provided with two stems—one for introducing air into the bladder and another for removing air from the bladder—without departing from the scope of this invention. Also, although the stem 62 has been described as having a particular type of valve construction, it is to be understood that any suitable valve construction could be employed without departing from this invention.

Referring now to FIGS. 1, 8 and 9, the brace structure 26 is removably insertable into the orthosis body 22 and is primarily used to initially set the degree of abduction. When inserted, the brace structure 26 maintains the leg engaging portions 28, 30 spaced apart even when the bladder 24 is deflated. The brace structure 26 comprises first (left) and second (right) generally rigid leg pressing members 68, 70 and a spacer structure, generally indicated at 72, for maintaining the leg pressing members spaced apart. Preferably, each leg pressing member 68, 70 has a concave outer surface 74 (FIG. 9) for applying a somewhat uniform pressure to the inner thighs of the patient P. The spacer structure comprises first (outer) and second (inner) telescoping tube sections 76, 78. The outer tube section 76 is connected at one end (i.e., its right most end as viewed in FIG. 8) to the left leg pressing member 68 via a first bracket 80. The inner tube section 78 is connected at one end (i.e., its left most end as viewed in FIG. 8) to the right leg pressing member 70 via a second bracket 82.

Preferably, a spring-biased lock button 84 is attached to the inner tube section 78 and extends radially outward therefrom (i.e., out of the page as viewed in FIG. 8). The lock button 84 is alignable with and adapted to extend through any one of a plurality of adjustment holes 86 through the outer tube section 76 to releasably lock the inner and outer tube sections 76, 78 together. Pushing the lock button 84 causes it to disengage from its corresponding adjustment hole 86 thereby allowing the tube sections 76, 78 to be telescoped in or out to adjust the spacing between the leg pressing members 68, 70. When the spring-biased button 84 is brought into alignment with another of the adjustment holes 86, then the button snaps outward and into the aligned hole to lock the tube sections 76, 78 together.

Referring again to FIGS. 1, 3 and 7, the intermediate portions 42 of the leg engaging portions 28, 30 and the bladder receiving pocket 32 define first (left) and second (right) brace pockets 88, 90 for receiving the leg pressing members 68, 70 of the spacer structure 72. The left brace pocket 88 is between the left leg engaging portion 28 and the bladder receiving pocket 32 and is sized and configured for receiving the left leg pressing member 68. The right brace pocket 90 is between the right leg engaging portion 30 and the bladder receiving pocket 32 and is sized and configured for receiving the right leg pressing member 70. The panels defining the brace pockets 88, 90 are shown in FIG. 7 as being spaced apart. However, it is to be understood that these panels will be squeezed together between the bladder 24 and the legs of the patient to close the spacing when the leg pressing members 68, 70 are withdrawn from the brace pockets 88, 90 and when the patient is wearing the orthosis 20.

To provide abduction to legs or thighs of the patient, the orthosis body 22 is positioned between the thighs of the patient. The straps 40 of the leg engaging portions 28, 30 are then looped around the patient's thighs so that the hook-type fasteners 44 of the straps engage the loop-type fasteners 46 of the flaps 38 to secure the leg engaging portions to the patient's legs. The bladder 24 may be inserted into the bladder receiving pocket 32 either before or after the orthosis body 22 is secured to the patient's legs. However, the bladder 22 is preferably kept deflated until after the orthosis body 22 is secured to the legs to minimize the extent to which the patient's legs must be spread during emplacement of the orthosis 20. After emplacement, the bladder 24 is slowly inflated and expanded with air to gently increase the spacing between the leg engaging portions 28, 30 and to gently increase the spread of the patient's legs until the desired extent of abduction is achieved. When inflated, the bladder presses against the inner thighs of the patient P, via the bladder receiving pocket 32 and leg engaging portions, to maintain the legs of the patient spread apart. The extent of abduction (i.e., the extent to which the patient's legs are spread) may be easily adjusted by either adding more air into or removing air from the bladder with minimal disruption to the patient. The flexibility of both the orthosis body 22 and the bladder 24 causes the leg engaging portions 28, 30 and the bladder to conform to the shape of the patient's legs, e.g., to a shape substantially as shown in FIG. 4. Because of this conformity, the abduction force imparted to the legs of the patient by the orthosis 20 will be distributed over a substantially large area. Thus, the orthosis 20 avoids imparting localized pressure points to the legs of the patient.

The orthosis body 22 and bladder 24 (without the brace structure 26) are sufficient to provide abduction to the legs of a patient. Thus, in some situations it may be advantageous to refrain from using the brace structure. However, in other situations it may be advantageous to use the brace structure 26 at least to initially set to degree (extent) of abduction. In other words, the brace structure 26 may be employed with the orthosis body 22 to set the desired extent of abduction even before the bladder 24 is inflated.

If it is desired to use the brace structure 26 with the orthosis body 22 and bladder 24, the leg pressing members 68, 70 of the brace structure may be inserted into the brace pockets 88, 90 either before inflation or after partial inflation of the bladder, but preferably after the leg engaging portions 28, 30 are attached to the legs. When the brace structure 26 is properly positioned, it maintains a desired spacing between the left and right leg engaging portions 28, 30 to maintain the desired abduction to the legs of the patient. In particular, the leg pressing members 88, 90 of the brace structure 26 press against the intermediate portions 42 of the leg engaging portions 28, 30, which in turn press against the inner thighs of the patient. After the brace structure 26 is properly positioned and the desired abduction is achieved, then the bladder 24 maybe inflated. After the bladder 24 is inflated, then the brace structure 26 may be removed.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense. The invention therefore shall be limited solely by the scope of the claims set forth below.

What is claimed:

1. An orthosis for providing abduction to legs of a patient comprising:

first and second leg engaging portions configured for operatively engaging first and second legs of the patient, the first and second leg engaging portions comprising first and second thigh engaging portions configured for operatively engaging first and second thighs of the patient, the leg engaging portions being configured for attachment of the orthosis to the patient's legs;

at least one inflatable bladder generally between and operatively attached to the leg engaging portions, the bladder having at least one port for introducing fluid into and removing fluid from the bladder thereby to inflate and deflate the bladder; and a bladder receiving pocket generally between and attached to the thigh engaging portions, the bladder receiving pocket being configured for holding the bladder;

the bladder being positioned relative to the first and second leg engaging portions so that the bladder resists movement of the leg engaging portions toward each other when the bladder is inflated to maintain the first and second leg engaging portions spaced apart and thereby to maintain the legs of a patient wearing the orthosis spread apart.

2. An orthosis as set forth in claim 1 wherein the first and second leg engaging portions are configured for attachment of the orthosis to the patient's thighs.

3. An orthosis as set forth in claim 2 wherein each leg engaging portion comprises a flap connected to the bladder receiving pocket and a strap connected to the bladder receiving pocket, the strap being configured to be looped around a corresponding one of the thighs of the patient so that an end margin of the strap overlaps the flap.

4. An orthosis as set forth in claim 1 wherein the bladder receiving pocket has an opening for removal of the bladder from and insertion of the bladder into the bladder receiving pocket.

5. An orthosis as set forth in claim 4 wherein the opening is sufficiently large to permit insertion of the bladder into and removal of the bladder from the bladder receiving pocket when the bladder is in a deflated condition and sufficiently small to prevent such insertion and removal when the bladder is in an inflated condition.

6. An orthosis as set forth in claim 4 wherein the bladder receiving pocket is of a flexible sheet material.

7. An orthosis as set forth in claim 6 wherein the bladder receiving pocket comprises first and second portions adjacent the opening, and first and second mateable fastener elements attached to the first and second portions, respectively, the first and second fastener elements being located on the first and second portions of the bladder receiving pocket such that the first and second portions are held generally together by the fastener elements to thereby close the opening when the first fastener element mates with the second fastener element.

8. An orthosis as set forth in claim 1 wherein the bladder is shaped and configured such that adding fluid to the bladder increases the distance between the leg-engaging portions, and removing fluid from the bladder decreases the distance between the leg-engaging portions.

9. An orthosis as set forth in claim 1 wherein the bladder is configured such that its volume increases when fluid is added thereto and decreases when fluid is removed therefrom thereby to vary the spacing between the first and second leg engaging portions and to vary the degree of spread of the patient's legs when the patient is wearing the orthosis.

10. An orthosis as set forth in claim 1 wherein the bladder receiving pocket and leg engaging portions comprise an orthosis body, the orthosis further comprising a brace structure at least a part of which is insertable into the orthosis body generally between the first and second leg engaging portions to maintain the leg engaging portions spaced apart even when the bladder is deflated.

11. An orthosis as set forth in claim 10 wherein the brace structure comprises first and second generally rigid leg pressing members engageable with the first and second leg engaging portions, and a spacer structure for maintaining the first and second leg pressing members spaced apart.

12. An orthosis as set forth in claim 11 wherein the orthosis body further comprises a first brace pocket generally between the first leg engaging portion and the bladder receiving pocket, and a second brace pocket generally between the second leg engaging portion and the bladder receiving pocket, the first brace pocket being configured for receiving the first leg pressing member, the second brace pocket being configured for receiving the second leg pressing member.

13. An orthosis for providing abduction to a patient's legs, the improvement comprising a fluid filled bladder positionable between the patient's legs, and a removable rigid brace structure configured for selective insertion between the patient's legs to thereby structurally establish a minimum degree of abduction.

14. The orthosis of claim 13 wherein said bladder includes a port through which fluid may be introduced into and removed from said bladder.

15. The orthosis of claim 13 wherein said brace structure includes an adjustable strut to thereby change the degree of abduction.

16. An orthosis for providing abduction to legs of a patient, comprising:
first and second thigh engaging portions configured for operatively engaging first and second thighs of a patient;
at least one bladder generally between and operatively attached to the thigh engaging portions, the bladder having at least one port for filling the bladder with fluid and emptying the bladder of fluid; and
a bladder receiving pocket generally between and attached to the thigh engaging portions, the bladder receiving pocket being configured for holding the bladder, the bladder receiving pocket having an opening for removal of the bladder from and insertion of the bladder into the bladder receiving pocket;
the bladder being positioned relative to the first and second thigh engaging portions so that the bladder resists movement of the thigh engaging portions toward each other when the bladder is filled with fluid to maintain the first and second thigh engaging portions spaced apart and thereby to maintain the thighs of a patient wearing the orthosis spread apart.

17. An orthosis as set forth in claim 16 wherein the opening is sufficiently large to permit insertion of the bladder into and removal of the bladder from the bladder receiving pocket when the bladder is in an empty condition and sufficiently small to prevent such insertion and removal when the bladder is in a fluid filled condition.

18. An orthosis as set forth in claim 16 wherein the thigh engaging portions are configured for attachment of the orthosis to the patient's thighs.

19. An orthosis as set forth in claim 16 further comprising a brace structure positionable generally between the first and second thigh engaging portions to maintain the thigh engaging portions spaced apart even when the bladder is empty.

20. An orthosis as set forth in claim 19 wherein the brace structure comprises first and second generally rigid thigh pressing members engageable with the first and second thigh engaging portions, and a spacer structure for maintaining the first and second thigh pressing members spaced apart.

21. An orthosis as set forth in claim 20 wherein the thigh engaging portions are configured for attachment of the orthosis to the patient's thighs.

22. An orthosis as set forth in claim 20 wherein each thigh engaging portion comprises a flap connected to the bladder receiving pocket and a strap connected to the bladder receiving pocket, the strap being configured to be looped around a corresponding one of the thighs of the patient so that an end margin of the strap overlaps the flap.

23. An orthosis as set forth in claim 20 wherein the bladder receiving pocket and thigh engaging portions comprise an orthosis body, the orthosis further comprising a brace structure at least a part of which is insertable into the orthosis body generally between the first and second thigh engaging portions to maintain the thigh engaging portions spaced apart.

24. An orthosis as set forth in claim 23 wherein the brace structure comprises first and second generally rigid thigh pressing members engageable with the first and second thigh engaging portions, and a spacer structure for maintaining the first and second thigh pressing members spaced apart.

25. An orthosis as set forth in claim 24 wherein the orthosis body further comprises a first brace pocket generally between the first thigh engaging portion and the bladder receiving pocket, and a second brace pocket generally between the second thigh engaging portion and the bladder receiving pocket, the first brace pocket being configured for receiving the first thigh pressing member, the second brace pocket being configured for receiving the second thigh pressing member.

* * * * *